United States Patent [19]

Tarzian

[11] Patent Number: 5,098,408
[45] Date of Patent: Mar. 24, 1992

[54] AUTOMATIC INTRAVENOUS FLOW CONTROLLER

[75] Inventor: George M. Tarzian, Chicago, Ill.

[73] Assignee: General Automatic Corp., Rolling Meadows, Ill.

[21] Appl. No.: 478,559

[22] Filed: Feb. 12, 1990

[51] Int. Cl.5 .................................................. A61M 5/00
[52] U.S. Cl. ................................. 604/248; 251/125; 604/251
[58] Field of Search .................. 604/246–248, 604/251–253, 65, 67; 137/508; 251/125

[56] References Cited

U.S. PATENT DOCUMENTS

| | | | |
|---|---|---|---|
| 2,935,088 | 5/1960 | Thompson et al. | 137/613 |
| 3,021,841 | 2/1962 | Burke | 128/214 |
| 3,101,710 | 8/1963 | Koehn | 128/214 |
| 3,163,176 | 12/1964 | Darling | 137/487.5 |
| 3,323,774 | 6/1967 | Wilson | 251/125 |
| 3,332,439 | 7/1967 | Burke | 137/556 |
| 3,587,313 | 6/1971 | Smith | 73/209 |
| 3,785,378 | 1/1974 | Stewart | 251/125 X |
| 3,893,468 | 7/1975 | McPhee | 137/1 |
| 4,079,737 | 3/1978 | Miller | 128/214 R |
| 4,141,379 | 2/1979 | Manske | 137/496 |
| 4,227,525 | 10/1980 | Lundquist | 604/252 X |
| 4,238,108 | 12/1980 | Muetterties | 251/6 |
| 4,261,356 | 4/1981 | Turner et al. | 128/214 R |
| 4,261,388 | 4/1981 | Shelton | 137/486 |
| 4,300,552 | 11/1981 | Cannon | 128/214 E |
| 4,317,473 | 3/1982 | Gaydos | 604/251 X |
| 4,343,305 | 8/1982 | Bron | 604/248 |
| 4,383,252 | 5/1983 | Purcell et al. | 340/606 |
| 4,387,734 | 6/1983 | Borsanyi | 251/125 X |
| 4,447,226 | 5/1984 | Mayoral | 604/73 |
| 4,634,434 | 1/1987 | Marino, Jr. et al. | 604/246 |
| 4,687,473 | 8/1987 | Raines | 604/246 X |
| 4,738,665 | 4/1988 | Shepard | 604/248 |
| 4,744,786 | 5/1988 | Hooven | 604/246 |
| 4,802,506 | 2/1989 | Aslanian | 604/246 X |
| 4,874,386 | 10/1989 | O'Boyle | 604/248 X |

Primary Examiner—C. Fred Rosenbaum
Assistant Examiner—C. Maglione
Attorney, Agent, or Firm—Patula & Associates

[57] ABSTRACT

An intravenous flow controller having inlet and outlet ends. An icicle or stylus drop former is positioned in fluid communication between the inlet end and the outlet end. A diaphragm in fluid communication with said inlet ends and the icicle drop former. A collection tube for collecting drops of fluid from the icicle drop former. A flow variation device for controlling flow of aggregate drops collected in the collection tube to the outlet end.

25 Claims, 8 Drawing Sheets

| FIG.7 |
| FIG.8 |
| FIG.9 |

AUTOMATIC INTRAVENOUS FLOW CONTROLLER

This invention relates to the improvement of intravenous flow devices. In particular the invention allows the flow rate of fluids entering the body to be accurately and quickly determined regulated and monitored to eliminate the flow variation problems caused by varying fluid level and to consolidate all flow control components into one integral housing.

BACKGROUND OF THE INVENTION

Intravenous devices are vital instruments for many medical procedures. Intravenous devices, or "I.V.'s" transport parenteral solutions (e.g., solutions containing antibiotics) into the body when physical ingestion is not possible or not as efficient. Before this invention, precise regulation of the fluid or solution flow was a time-consuming process which required counting and timing the flow drops. This invention allows a medical technician or nurse to precisely regulate the I.V. flow rate in a matter of seconds. It also allows doctors and following care personnel to instantly view the flow rate set by the prior care giving shift.

One of the most inventive features of the present invention is the use of a diaphragm and drop former stylus or icicle for highly accurate and graduated reproducible flow results. Because I.V. systems operate at micro pressure ranges, even the smallest resistance in the fluid path can cause inaccuracy in the fluid flow rate. The present invention achieves a high degree of flow freedom with limited flow restriction. Because capillary attraction plays an important hydrostatic role in the flow of aqueous solutions at micro pressures, the drip stylus coacts with capillary attraction to assure an accurately formed globule from drop to drop even if the controller is at an "off vertical" attitude.

The present invention is further novel, in that since atmospheric pressure also plays an important role in low pressure fluid dynamics, the fluid passages are configured for low resistance passage of fluid eliminating choke junctures and the like.

Numerous devices have been developed for gravitational fluid I.V. fluid systems claiming to be accurate not only in drop rate but also in flow control. Many of these devices rely on the time-consuming and inaccurate process of counting the drips in a drip chamber to regulate flow such as those shown in McPhee, U.S. Pat. No. 3,893,468; Shelton, U.S. Pat. No. 4,261,388; Smith, U.S. Pat. No. 3,587,313. Some devices use monitors which simply register and display the flow rate such as Purcell, U.S. Pat. No. 4,383,252; Koehn, U.S. Pat. No. 3,101,710; Darlino, U.S. Pat. No. 3,163,176. Other devices utilize complicated flow control valves which do not approach the accuracy of the present invention and utilize different structure and mechanisms for control such as shown in Miller, U.S. Pat. No. 4,079,737; Marino, U.S. Pat. No. 4,634,434; Wilson, U.S. Pat. No. 3,237,774; Manske, U.S Pat. No. 4,141,379; Burke, U.S. Pat. No. 3,021,841; Mavoral, U.S. Pat. No. 4,447,226.

Over the years, various devices to control flow, such as in Burke, U.S. Pat. No. 3,021,841, Darlino, U.S. Pat. No. 3,163,176, Cannon, U.S. Pat. No. 4,300,552 and Thompson, U.S. Pat. No. 2,935,088 had been developed but without concern for a high level of accuracy and by utilizing complicated mechanisms entirely different from the present invention.

An invention such as that shown in Bron, U.S. Pat. No. 4,343,305 is unable to accurately control the formation of drop and must be positioned absolutely vertical at all times in order to have an accurate flow or virtually any flow. Furthermore, the device in Bron is not an integrated system therefore having less accuracy and control than the present invention and utilizes a different flow control system with different structure.

The structures shown in McPhee, U.S. Pat. No. 3,843,468, Shelton, U.S. Pat. No. 4,261,388 and in Burke, U.S. Pat. No. 3,332,439 utilize an adjustable clamping device applied to the tubing. The present invention's intent is to avoid such inaccurate mechanisms.

Other devices such as that described in Koehn, U.S. Pat. No. 3,101,710 disclose a flow meter to provide accurate readings but must rely on the other devices for monitoring flow control.

Mayoral, U.S. Pat. No. 4,447,226 and Miller, U.S. Pat. No. 4,079,737 utilize complicated valve mechanisms but are unable to achieve the accurate flow calibration and regulation of the present invention.

It is a principal object of the present invention to provide a intravenous flow controller which automatically compensates for the variances in fluid flow rates caused between full, partially full or almost empty I.V. fluid source containers.

It is another object of the present invention to form droplets of consistent volume by controlling the size and shape of the droplets.

It is a further object of the present invention to visually set by a physical indicator the regulated flow rate of the fluid to be passed through the inventive flow controller and injected into the patient.

It is another object of the present invention to utilize a check valve system to replace the fluid passed into the controller with the displaced gas by returning the same to the source container in relative proportions.

It is yet another object of the present invention to have a regulation indicator device and a separate turn off device allowing for the stoppage of flow while temporarily moving the patient, etc. without changing the flow regulation setting of the device.

The present invention obviates all known prior devices by a simple, economical to fabricate I.V. flow controller which can be disposed of after a single use and does not involve complicated assembly nor specialized materials. It's ease of use, maintenance, safety and fluid flow accuracy cannot be overlooked.

Numerous other advantages and features of the invention will become readily apparent from the detailed description of the preferred embodiment of the invention, from the claims, and from the accompanying drawings, in which like numerals are employed to designate like parts throughout the same.

BRIEF SUMMARY OF THE INVENTION

An automatic intravenous flow controller which has a graduated flow control which allows the user to set via an indicator the flow rate from an intravenous solution container through the flow device into the patient. The controller of the present invention automatically compensates for the differences in flow rates caused by varying fluid levels in the source container. The use of a conical drop former provides a consistent sized drop regardless of rate of fluid passage and/or the amount of source fluid. The inventive controller is simple in design and is disposable.

DETAILED DESCRIPTION OF THE PREFERRED EMBODIMENT OF THE INVENTION

While the invention is susceptible of embodiment in many different forms there is shown in the drawings and will be described herein in detail, a preferred embodiment of the invention. It should be understood, however, that the present disclosure is to be considered an exemplification of the principles of the invention and is not intended to limit the spirit and scope of the invention and/or claims of the embodiment illustrated.

Figure 1:
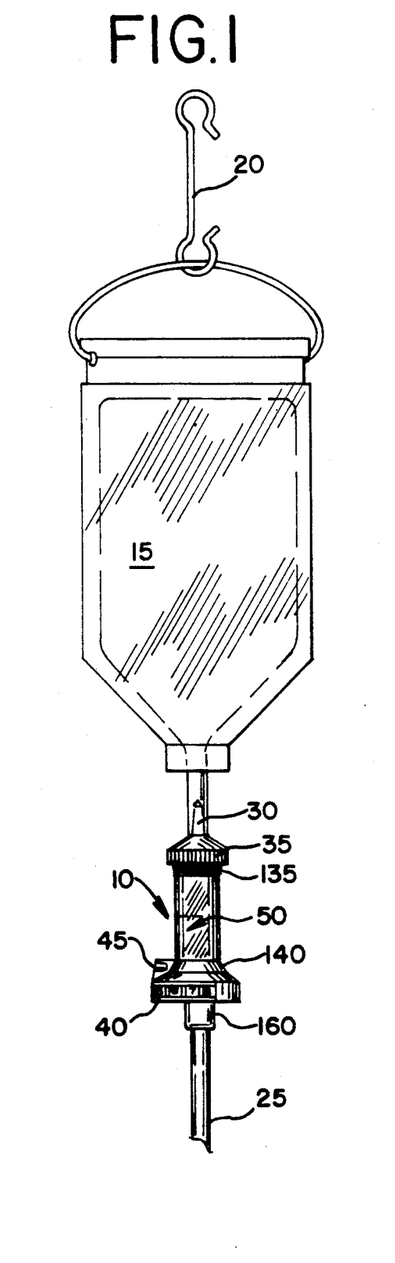
FIG. 1 is a perspective view of the automatic intravenous flow controller of the present invention in use with a typical intravenous application.

Shown in FIG. 1 is the present invention flow controller 10 as used in an intravenous fluid injection system having a fluid container or source 15 which is supported against gravity by a conventional support means or hook 20. It is expected that the source 15 be higher in relative elevation from the flow controller 10 to utilize the effect of gravity to transmit the fluid contained therein in the flow controller 10 and to an outlet passage tube 25. The flow controller 10 is shown with an inlet end 30, flow stoppage indicator 35, upper collar 135, collection tube 50, I.V. inlet port 45 in lower diaphragm housing 140 with graduated flow indicator 40 mounted on thumb wheel housing 160.

Figure 2:
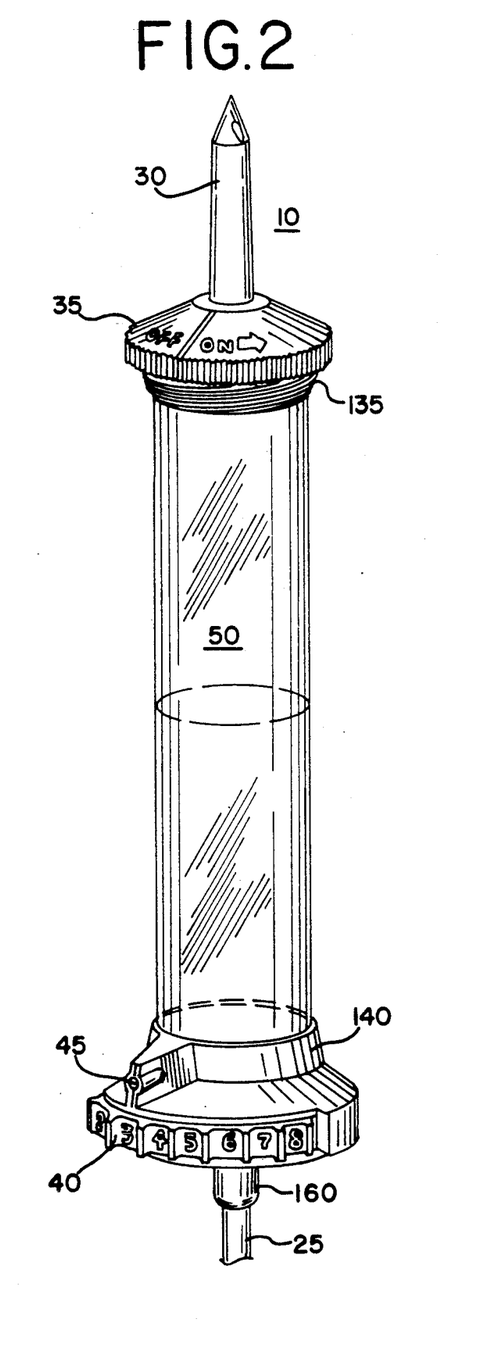
FIG. 2 is a perspective view of the automatic intravenous flow controller shown in FIG. 1.

FIG. 2 depicts the flow controller 10 having a fluid inlet end 30 with a rotatable flow stoppage indicator 35 mounted on upper collar 135. Indicator 35 indicates whether or not the flow controller 10 is operable or allows fluid to flow. Collection tube 50 is shown as a cylindrical tube in which visual indication is possible through the transparent sides of the tube. An IV inlet port 45 is positioned on lower diaphragm housing 140 at the gravity lower end of collection tube 50. Inlet port 45 allows for the injection of auxiliary fluids into collection tube 50. A graduated flow indicator 40 indicates a preset pre-calibrated flow rate of fluid collected in collection tube 50 through thumb wheel housing 160 to outlet passage tube 25.

Figure 3:
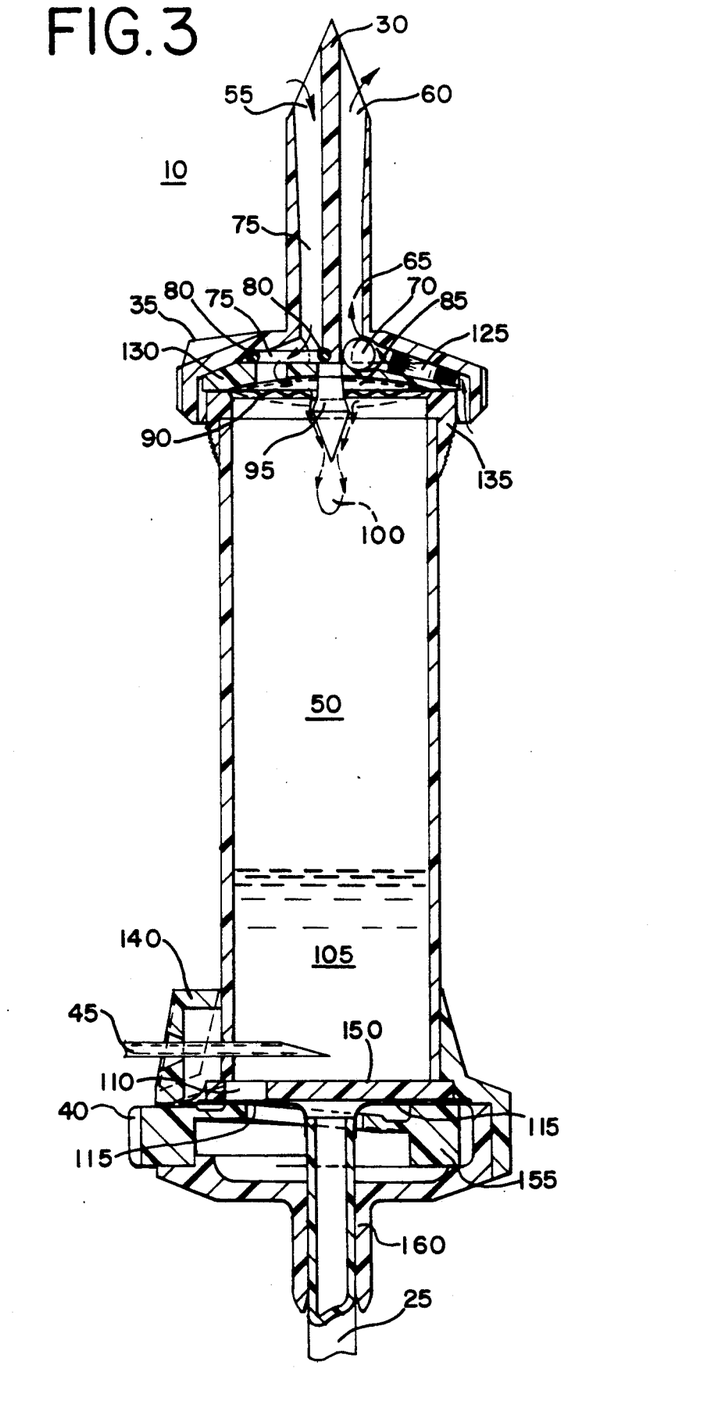
FIG. 3 is a cross-sectional view of automatic intravenous flow controller shown in FIG. 1.

Shown in FIG. 3 is the flow controller device 10 in which inlet end 30 is depicted having two ports, a fluid inlet port 55 and a pressure of equalization port 60. Fluid inlet port 55 creates an inlet flow passageway 75 which flows into fluid inlet chamber 85 via fluid inlet flow passageway 75 and pass through resilient deformable seal 80 in drip needle disc 130 which fits within upper collar 135.

Upon entering fluid inlet chamber 85, the fluid is in contact with convoluted diaphragm 90 and stylus or icicle drop former 95. A drop passes through convoluted diaphragm 90 and forms a drop on drop former 95. An accurately and repeatedly formed or shaped drop 100 is shown therein. Environmental atmospheric pressure is equalized to a source 15 (not shown) via equalization passageway 65 variable density breather filter 125 and check valve mechanism 70 through pressure equalization port 60.

Drops 100 formed on drop former 95 are collected in collection tube 50 and shown in aggregate as collected fluid 105. An I.V inlet port 45 mounted on lower diaphragm housing 140 is showing an access into collection tube 50. Graduated flow control outlet 110 is shown in metering plate 150 allowing to be in fluid communication with outlet flow diaphragm 115 and into middle flow housing 155 which is helical in shape or spiral ramp type. Graduated flow indicator 40 is part of middle flow housing 155 which correlates to regulate flow with thumb wheel housing 160.

Figure 4:
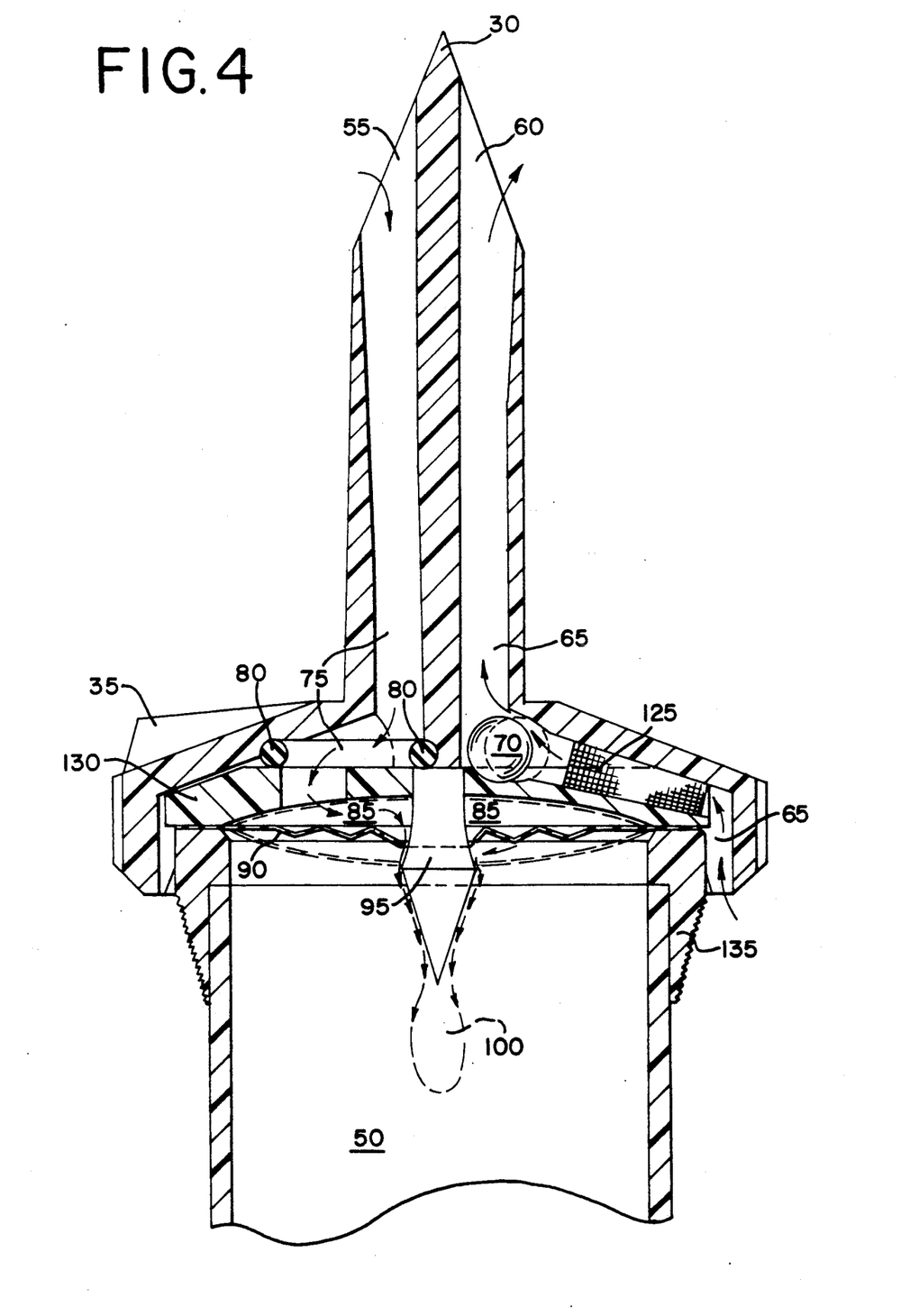
FIG. 4 is a partial cross-sectional view of the inlet end of the automatic intravenous flow controller shown in FIG. 1.
Figure 5:
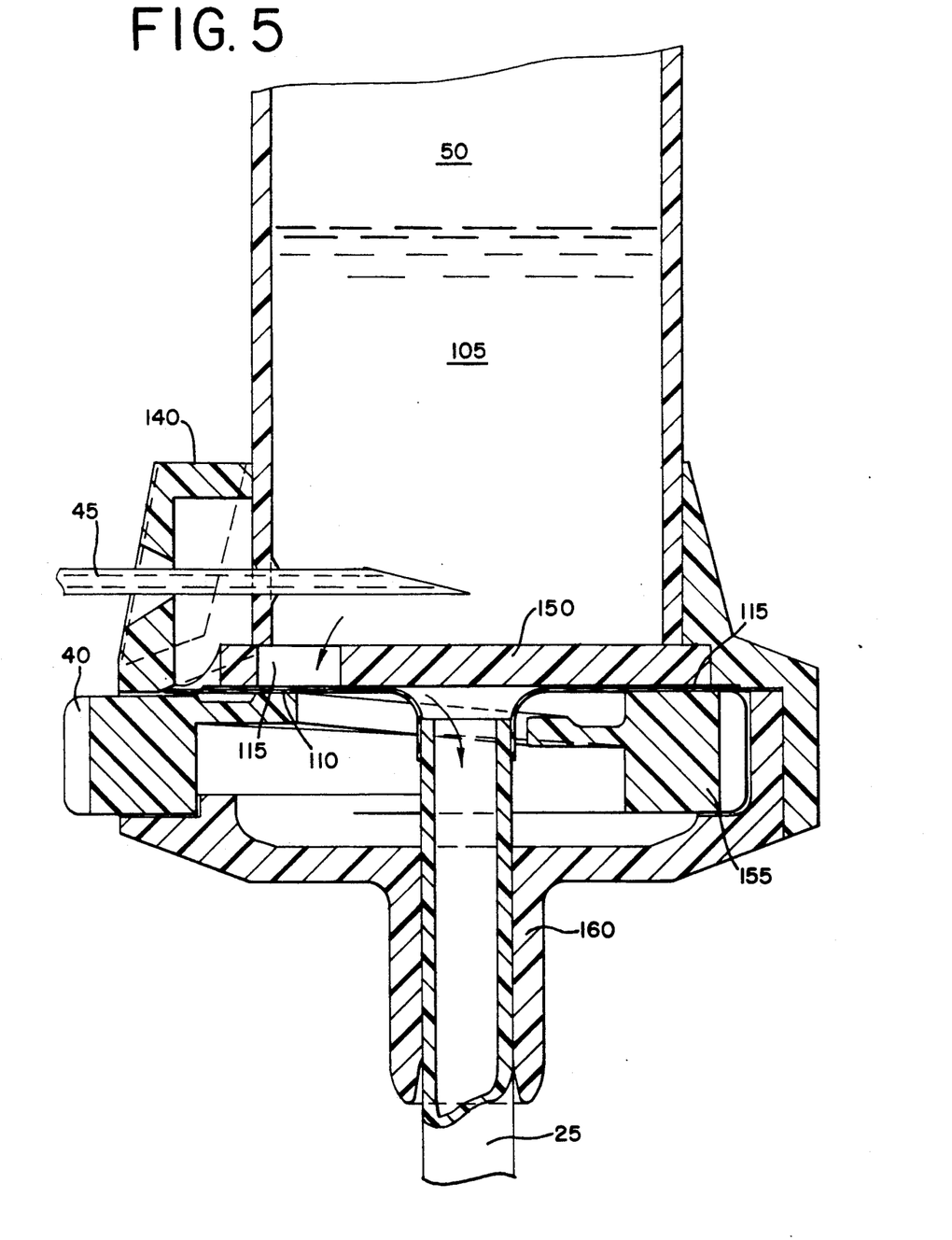
FIG. 5 is partial cross-sectional view of the outlet end of automatic intravenous flow controller shown in FIG. 1.

The operation and advantages of the present invention will become readily apparent by the fluid flow analysis shown in FIGS. 4 and 5.

Figure 6:
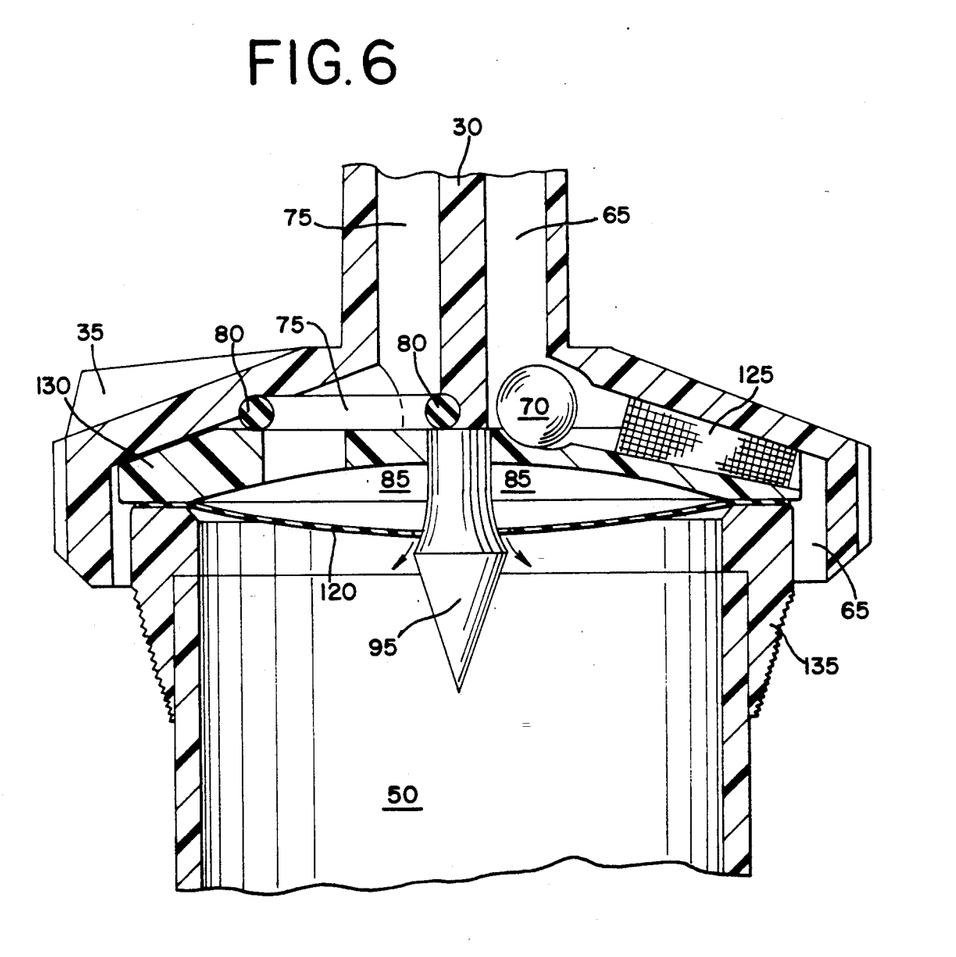
FIG. 6 is partial cross-sectional view of the inlet end of the automatic intravenous, flow controller shown in FIG. 1.

In FIG. 4 fluid to be injected into a patient from a source container 15 (not shown) enters inlet end 30 through fluid inlet port 55 and travels down inlet flow passageway 75 through flow stoppage indicator 35 and is prevented from leaking by resiliently deformable seal 80 which may be an 0-ring or other suitable seal. The fluid flows through and into drip needle disc 130 which is within upper collar 135 into chamber 85 and comes into contact with icicle drop former 95 and convoluted diaphragm 90 (or non-convoluted diaphragm 120 as shown in FIG. 6 in the alternative embodiment). The fluid flows through the center metering hole of diaphragm 90 (or in the alternative embodiment, non-convoluted diaphragm 120) along the arcuate surface of icicle drop form 95 as shown by the arrows in FIG. 4 to produce representative drop 100. The convoluted diaphragm 90 will be variably stretched (as shown in phantom) slowly removing or lessening the folds in the diaphragm depending on the pressure from up the flow path based on the amount of fluid in the source container. This varying of the diaphragm (likewise in FIG. 6 with alternate non-convoluted diaphragm 120) compensates for the varying fluid flow pressure created by the lessening of fluid level in the source thereby affording highly accurate flow rate control. The varying diaphragm 90 coupled with a icicle drop former 95 provides superior accuracy. It is also the intent of the present invention to utilize a combination of non-convoluted and convoluted thickness varying features of a diaphragm to achieve flow accuracy.

As the fluid level in a source 15 varies, the pressure in the source is equalized to the environment via equalization passageway 65 which flows through variable density breather filter 125 and check valve mechanism 70 which prevents source fluid from passing through equalization passageway 65 through variable density breather filter 125 and out to the environment. As the fluid level in a source 15 lessens the flow of equalizing air through equalization passageway 65 and pressure equalization port 60 increases.

The breather filter 125 may be of a maximum porosity no greater than 1 micron in order to prevent entry of bacteria into the I.V. source 15. Since the porosity will increase to 10 microns or over, at the inlet end, free air movement into the I.V. source 15 is assured for pressure equalization. In order to maintain hydrostatic balance as the I.V. fluid source changes from full to empty state, the fluid flow gap changes accordingly between the center hole of the diaphragm 90 and the arcuate surface of the drip neck of the drop former 95.

In order to commence or halt fluid flow through inlet flow passageway 75, flow stoppage indicator 35 is rotated upon drip needle disc 130 of upper collar 135 which prevents source fluid from entering chamber 85 from inlet flow passageway 75.

Should there be a fluid flow reversal and a danger of medication entering upward through inlet flow passageway 75 and thus contaminating fluid source 15, diaphragm 90 (and/or diaphragm 120 in the alternative embodiment) will instantly snap upward into the domed contour of drip needle disc 130 to prevent movement of fluid through inlet flow passageway 75 and fluid inlet port 55.

Figure 8:
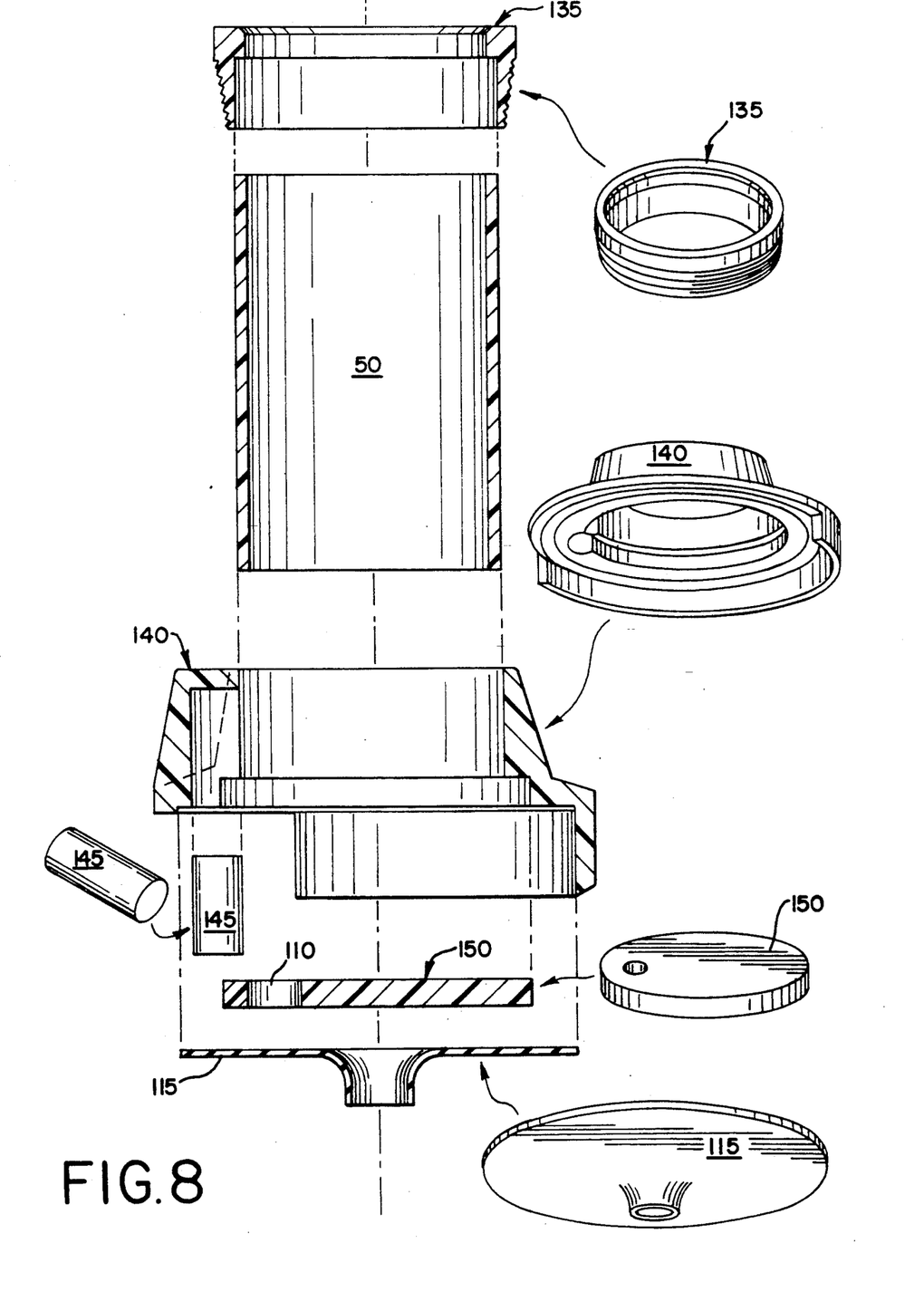

Representative drops 100 are released from icicle drop former 95 into collection tube 50 and as shown in FIG. 5 and collect as aggregate drops 105. Additional fluids may, if desired be injected into collection tube 50 via inlet port 45. (In FIG. 8 is shown a needle piercing plug 145 which affords the self sealing of port 45.) The aggregate drops or fluid 105 flow through outlet 110 in metering plate 150 and through outlet flow diaphragm 115 and into complementary helical ramps created by the interaction of middle flow housing 155 with numerical graduated flow indicator 40 and thumb wheel housing 160. The rotation of middle flow housing 155 between lower diaphragm housing 140 and thumb wheel housing 160 controls the size of the resulting fluid passageway and in turn the rate of flow out of flow controller device 10 into outlet passage tube 25.

In practical operation, a health care professional or nurse would insert inlet end 30 into a source 15 and connects an outlet flow tube between outlet passage tube 25 and to the administering patient. The nurse then rotates flow stoppage indicator 35 to "on" and visually views in collection tube 50, fluid released from drop former 95 and collected within the lower portion of collection tube 50. Upon collection of aggregate fluid in collection tube 50, the nurse may then rotate graduated flow indicator 40 to the desired flow rate setting.

FIG. 6 shown similar structure as that shown in FIG. 4 except in partial cross section wherein an alternate non-convoluted diaphragm 120 is shown therein.

Figure 7:
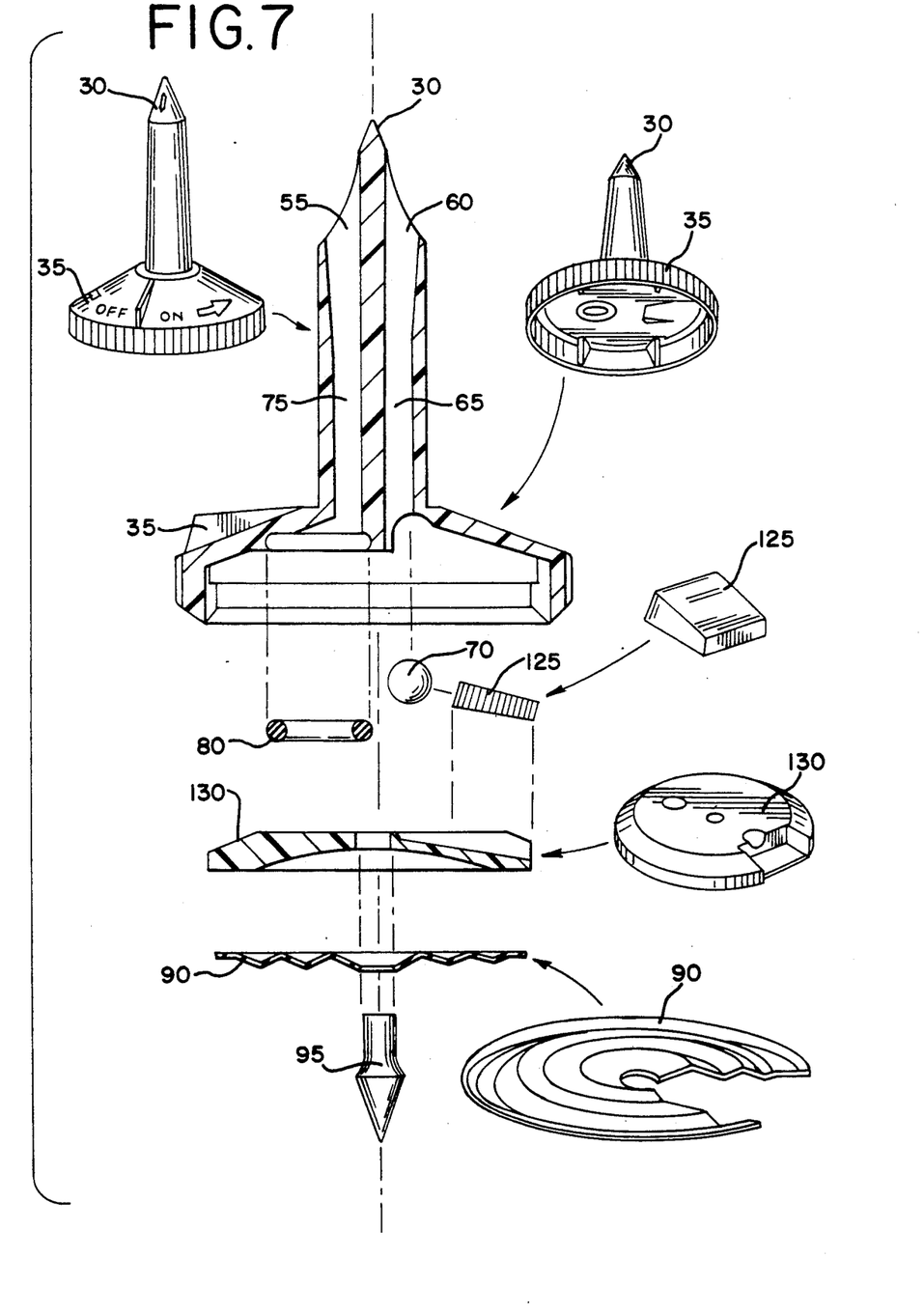
FIG. 7, 8 and 9 are exploded cross-sectional views of the invention shown in FIG. 1.
Figure 9:
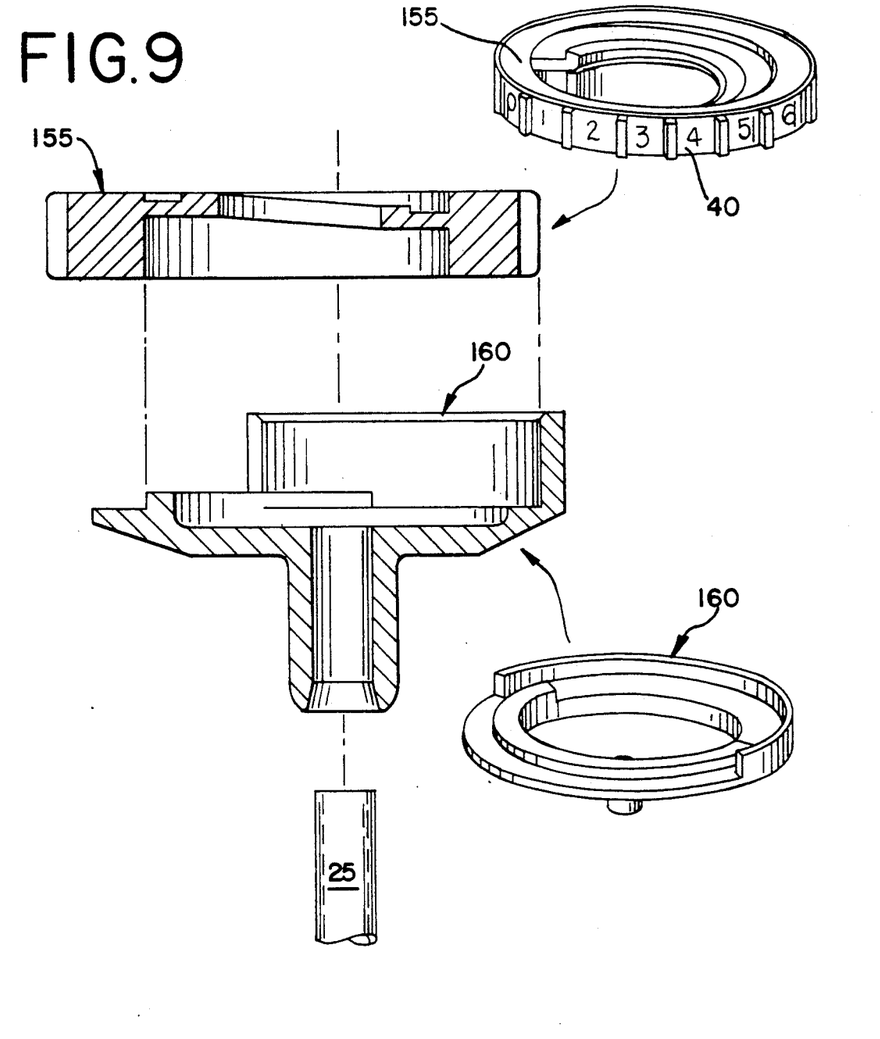
Figure 10:
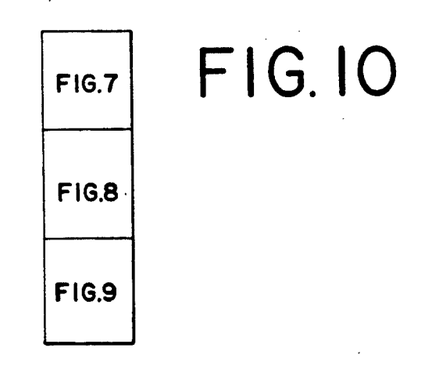
FIG. 10 is an assembly drawing of FIGS. 7-9.

FIG. 7, 8 and 9 show an exploded entire assembly diagram for the present invention as described above and combined as shown in FIG. 10.

The foregoing specification describes only the preferred embodiment of the invention as shown. Other embodiments besides intra venous may be articulated as well. The terms and expressions therefore serve only to describe the invention by example only and not to limit the invention. It is expected that others will perceive differences which while differing from the foregoing, do not depart from the spirit and scope of the invention herein described and claimed.

What is claimed is:

1. An intravenous flow controller, comprising:
   a fluid collection unit having an inlet end for receiving into said unit the fluid to be delivered intravenously, and an outlet end for passing said fluid out of said unit;
   means for forming droplets positioned in fluid communication between said inlet end and said outlet end;
   controller means for controlling the flow of fluid from out of said intravenous flow controller through said outlet end, said controller means positioned in fluid communication with said outlet and said droplet means; and
   diaphragm means positioned in fluid communication between said inlet and said droplet means in cooperative association with said droplet means for compensating for changes in fluid flow from said inlet end.

2. The intravenous flow controller of claim 1 wherein said diaphragm is of varying thickness.

3. The intravenous flow controller of claim 1 wherein said diaphragm is convoluted.

4. The intravenous flow controller of claim 1 wherein said flow variation means is an adjustable helical ramp flow passageway.

5. The intravenous flow controller of claim 4 wherein said flow variation means is graduated and has indications which correspond to pre-set calibrated fluid flow rates from said outlet end.

6. An intravenous flow controller for use with a fluid source, comprising:
   a fluid collection unit having an inlet end for receiving into said unit fluid to be delivered intravenously, and an outlet end for passing said fluid out of said unit, said inlet end having two ports in fluid communication with said fluid source; with a second port having a check valve means for compensating the pressure difference between the interior and exterior of said fluid source;
   an inlet flow diaphragm in fluid communication with said first port of said inlet end;
   icicle shaped means for forming drops of fluid in fluid communication with said diaphragm;
   collection means for collecting drops of fluid from said icicle shaped means and in fluid communication with said icicle shaped means;
   an outlet flow diaphrgam in fluid communication with said collection means; and
   flow variation means for controlling flow of aggregate drops collected in said collection means in fluid communication with said outlet flow diaphragm and to said outlet end.

7. The intravenous flow controller of claim 6, wherein said flow variation means is graduated with indications which correspond to pre-set calibrated fluid flow rates from said outlet end.

8. The intravenous flow controller of claim 6, wherein said inlet flow diaphragm is convoluted.

9. The intravenous flow controller of claim 6, wherein said inlet flow diaphragm is of varying thickness.

10. The intravenous flow controller of claim 6, wherein said collection means is available for visual inspection.

11. The intravenous flow controller of claim 6 further comprising a stoppage means for halting the flow of fluid to said inlet flow diaphragm, said stoppage means positioned between said first port of said inlet end and said inlet flow diaphragm.

12. The intravenous flow controller of claim 6 wherein said flow variation means is an adjustable helical ramp which modifies the shape of the flow passageway.

13. An intravenous flow controller for controlling and accurately regulating the flow of fluid from a source container to a patient, comprising:

a fluid collection unit having an inlet end for receiving into said unit fluid to be delivered intravenously, and an outlet end for passing said fluid out of said unit, said unit end having at least two ports and chamber means, with a first port in fluid communication with said fluid source and said chamber means for the passage of said fluid into said chamber means;

said chamber means having a permeable inlet diaphragm in fluid communication therein;

drop former means for forming drops of fluid, in fluid communication with said diaphragm being centered and through said diaphragm, said drop former means having a cylindrical shape outwardly converging to a maximum diameter point then conically extending to a termination point in the direction of fluid flow, said termination point being the departure of the drops of fluid;

collection means for collecting drops from said terminating point and having a first end and a second end, said collection means being coaxial over said chamber means and said drop former means at said first end;

outlet flow diaphragm in fluid communication; with said second end of said collection means;

graduated flow variation means in fluid communication with said second end of said collection means and said outlet flow diaphragm for controlling the rate of fluid flow of the drops collected in said collection means; and said outlet end further defined by being in communication with said graduated flow variation means and the patient.

14. The intravenous flow controller of claim 13 wherein said collection means affords visual observation of the drops released from said drop former means.

15. The intravenous flow controller of claim 13 wherein said inlet flow diaphragm regulates the flow of fluid through said inlet flow diaphragm in relation to the gravitational pressure created by the source fluid, which pressure varies depending upon varying volumes of said source fluid within said intravenous flow controller.

16. The intravenous flow controller of claim 15, wherein said graduated flow variation means is comprised of two complementary helically graduated rings which may be adapted against one another to control the fluid flow from said second end of said collection means to said outlet end.

17. The intravenous flow controller of claim 15 further comprising a stoppage means for halting the flow of fluid into said chamber means, said stoppage means in fluid communication with said first port of said inlet end and said chamber means.

18. The intravenous flow controller of claim 17, wherein said first port in said inlet end further comprising resiliently deformable seals to guard against unwanted source fluid flow from said stoppage means.

19. The intravenous flow controller of claim 15, wherein said graduated indexed/calibrated flow variation means is comprised of two complementary helically graduated rings which may be adapted against one another to control the fluid flow from said second end of said collection means to said outlet end.

20. The intravenous flow controller of claim 13, wherein said second port of said inlet is further defined by having a check valve mechanism to equalize the pressure into said source container but preventing the passage of source fluid from passing through said second port of said inlet end.

21. The intravenous flow controller of claim 13, wherein said inlet flow diaphragm has the ability to allow fluid flow only from said inlet end to said outlet end.

22. The intravenous flow controller of claim 13, wherein said inlet flow diaphragm is convoluted.

23. The intravenous flow controller of claim 13, wherein said inlet flow diaphragm is of varying thickness, wherein said diaphragm is 10 mils at said diaphragm's outer extremity and linearly decreasing to 2 mils at said diaphragm's epicenter.

24. The intravenous flow controller of claim 13, further comprising a stoppage means for halting the flow of fluid to said inlet flow diaphragm, said stoppage means positioned between said first port of said inlet end and said chamber means.

25. An intravenous flow controller for controlling and accurately regulating the flow of fluid from a source container to a patient, comprising:

a fluid collection unit having an inlet end for receiving into said unit fluid to be delivered intravenously, inlet an outlet end for passing said fluid out of said unit, said unit end having at least two ports and chamber means, with a first port in fluid communication with said fluid source and said chamber means for the passage of said fluid into said chamber means, a second port in fluid communication between the interior and exterior of the fluid source, said second port having a check valve mechanism to equalize the pressure between the interior and exterior of the fluid source;

said chamber means having a permeable inlet diaphragm in fluid communication with said chamber means which allows fluid to pass at a constant rate regardless of the amount of pressure extended by the fluid source;

drop former means for forming drops of fluid, in fluid communication with said diaphragm, said drop former means having a cylindrical shape outwardly converging to a maximum diameter point then conically extending to a termination point in the direction of fluid flow, and being centered and through said diaphragm at said maximum diameter point of said drop former means, said termination point commencing the departure of the droplets of fluid;

collection means for collecting drops from said terminating point and having a first end and a second end, said collection means being coaxial over said chamber means and said drop former means at said first end;

graduated calibrated controller means in fluid communication with said second end of said collection means for controlling the rate of the droplets collected in said collection means; and said outlet end further defined by being in communication with said graduated calibrated controller means and the patient wherein said controller means may be set to a desired flow rate by adjusting said graduated calibrated controller means.

* * * * *